United States Patent [19]
Seki et al.

[11] Patent Number: 5,485,382
[45] Date of Patent: Jan. 16, 1996

[54] OXYGEN SENSOR DETERIORATION-DETECTING SYSTEM FOR INTERNAL COMBUSTION ENGINES

[75] Inventors: Yasunari Seki; Toshihiko Sato; Naoki Iida; Yoichi Iwata, all of Wako, Japan

[73] Assignee: Honda Giken Kogyo K.K., Tokyo, Japan

[21] Appl. No.: 226,007

[22] Filed: Apr. 11, 1994

[30] Foreign Application Priority Data

Apr. 15, 1993 [JP] Japan .................................. 5-112329

[51] Int. Cl.$^6$ .............................. G06G 7/70; G06F 19/00; F01N 3/00
[52] U.S. Cl. .................. 364/431.05; 60/274; 60/276; 60/277; 60/285; 123/703; 123/688; 123/691; 123/692; 73/118.1; 364/431.03
[58] Field of Search .................. 60/276, 274, 277, 60/285, 60; 123/691, 692, 688, 694, 695, 674, 679, 682, 680; 364/431.01–431.12

[56] References Cited

U.S. PATENT DOCUMENTS

| | | | |
|---|---|---|---|
| 4,693,076 | 9/1987 | Chujo et al. | 60/274 |
| 5,074,113 | 12/1991 | Matsuoka | 60/285 |
| 5,154,054 | 10/1992 | Nakane et al. | 60/276 |
| 5,168,701 | 12/1992 | Yamamoto et al. | 60/276 |
| 5,207,057 | 5/1993 | Kayanuma | 60/276 |
| 5,228,287 | 7/1993 | Kuronishi et al. | 123/692 |
| 5,247,793 | 9/1993 | Yamada et al. | 123/691 |
| 5,251,604 | 10/1993 | Kaneko et al. | 123/688 |
| 5,279,114 | 1/1994 | Kurita et al. | 123/691 |
| 5,279,116 | 1/1994 | Shimizu et al. | 60/285 |
| 5,325,664 | 7/1994 | Seki et al. | 60/276 |
| 5,357,750 | 10/1994 | Ito et al. | 60/276 |

*Primary Examiner*—Kevin J. Teska
*Assistant Examiner*—Jacques H. Louis-Jacques
*Attorney, Agent, or Firm*—Arthur L. Lessler

[57] ABSTRACT

An oxygen sensor deterioration-detecting system for an internal combustion engine having a plurality of groups of cylinders groups, an exhaust system having a plurality of exhaust passages extending, respectively, from the cylinder groups, and catalytic converters arranged in the exhaust system, and a plurality of upstream oxygen sensors arranged, respectively, in the exhaust passages at locations upstream of the catalytic converters, includes a single downstream oxygen sensor arranged in a confluent portion of the exhaust passages at a location downstream of the catalytic converters, for detecting the mixed air-fuel ratio of exhaust gases emitted from the cylinder groups. An ECU is responsive to outputs from the upstream oxygen sensors and an output from the downstream oxygen sensor, for determining air-fuel ratio control amounts for respective ones of the cylinder groups, and for controlling the air-fuel ratios of air-fuel mixtures supplied into the respective cylinder groups by the use of the air-fuel ratio control amounts determined. The ECU detects deterioration of each upstream oxygen sensor, based on an output from the upstream oxygen sensor obtained by the air-fuel ratio control based on a corresponding one of the air-fuel ratio control amounts.

5 Claims, 12 Drawing Sheets

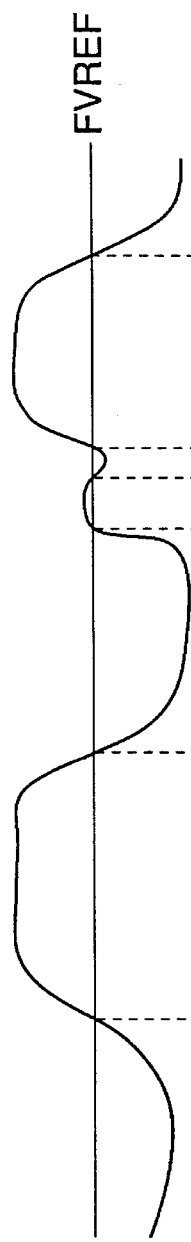
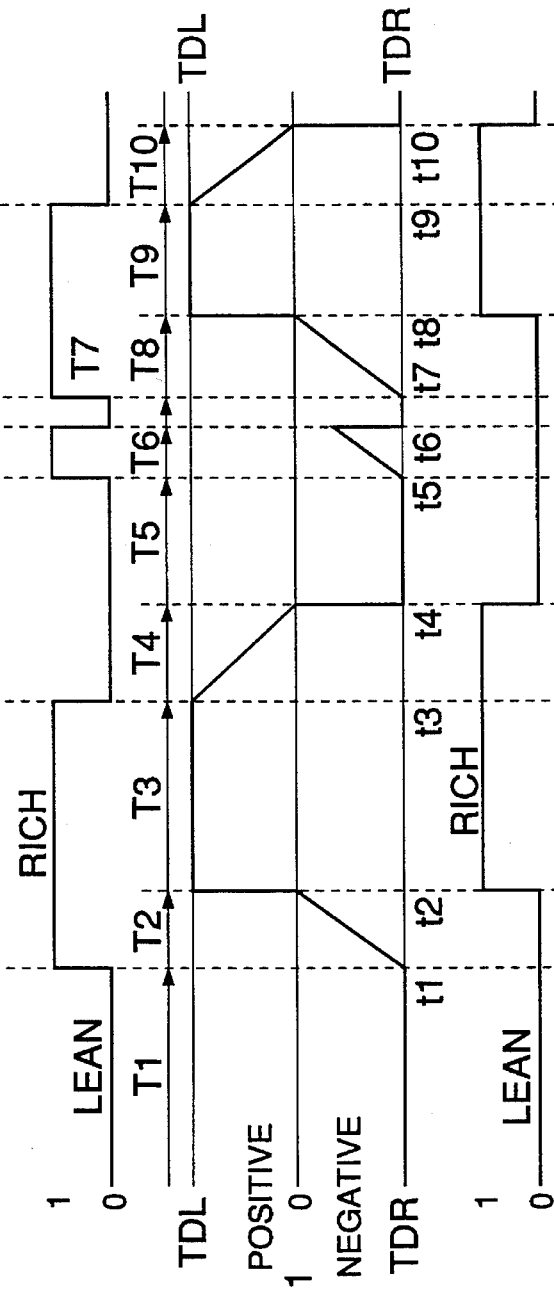
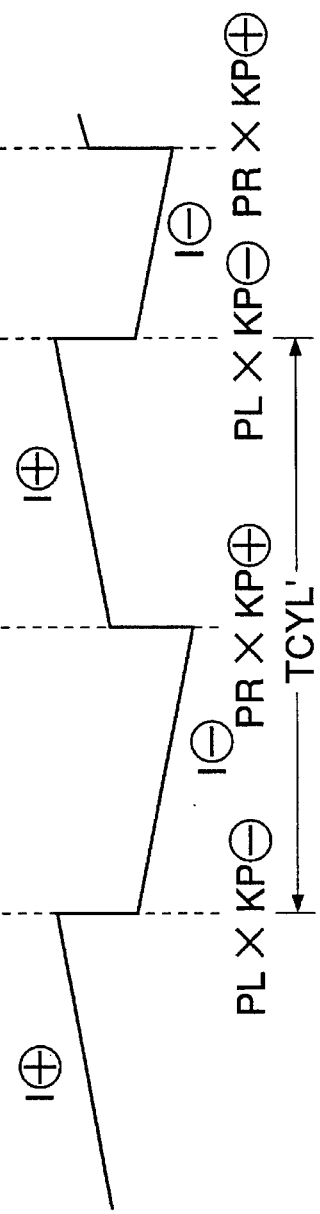
FIG.6A  R-FVO2
FIG.6B  FAF1
FIG.6C  CDLY1
FIG.6D  FAF2
FIG.6E  R-KO2

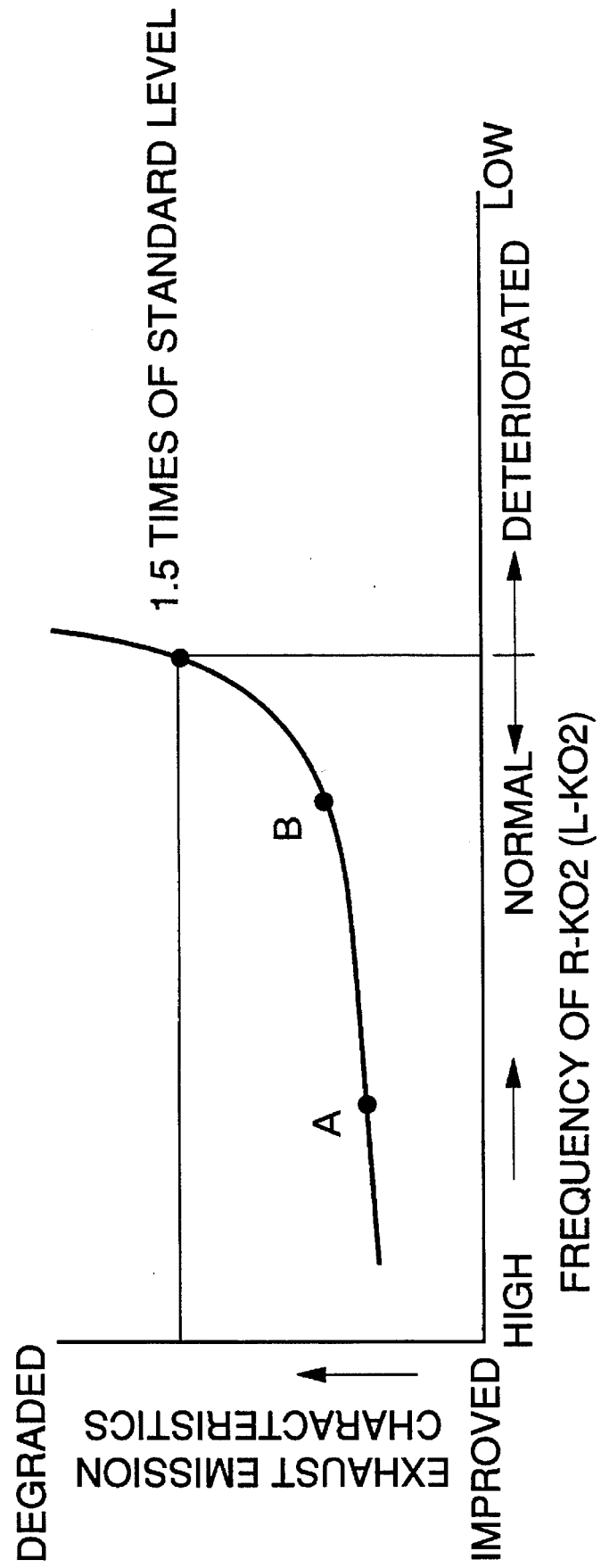

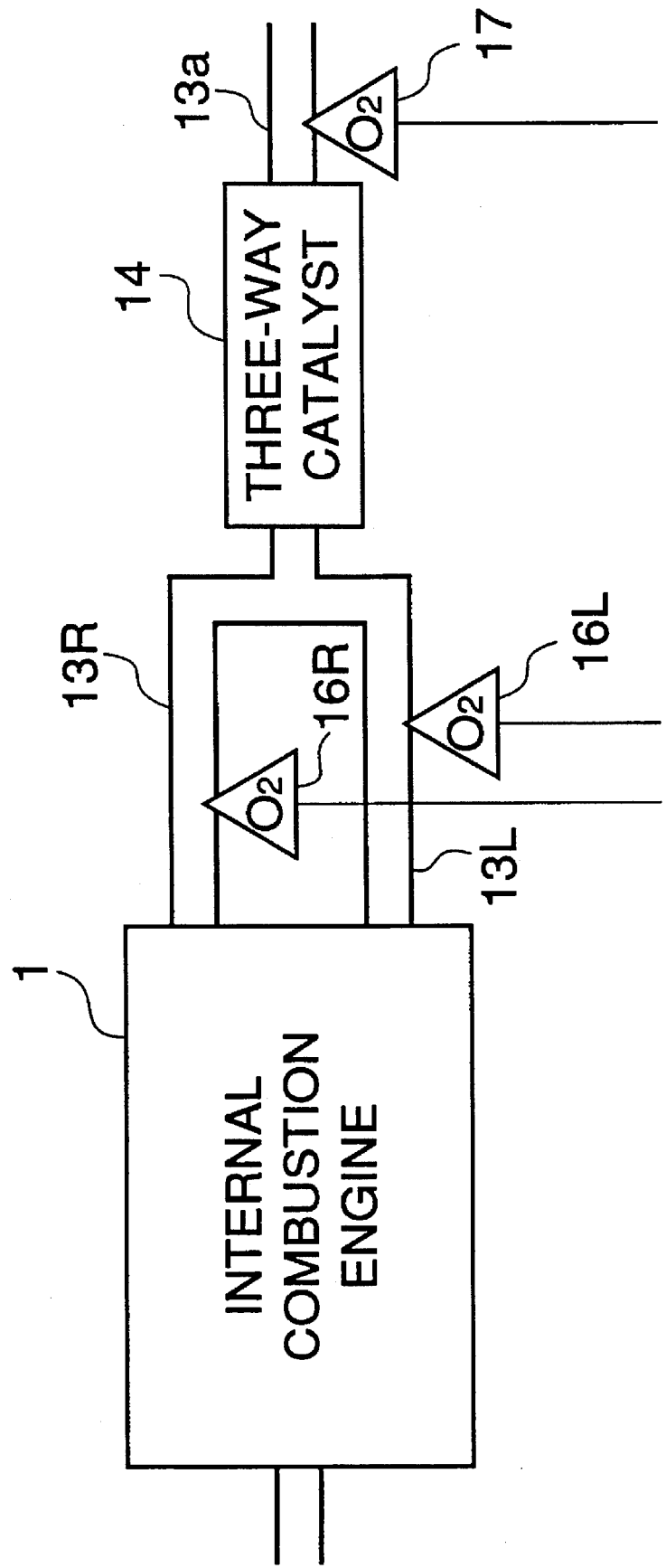

OXYGEN SENSOR DETERIORATION-DETECTING SYSTEM FOR INTERNAL COMBUSTION ENGINES

BACKGROUND OF THE INVENTION

1. Field of the Invention

This invention relates to an oxygen sensor deterioration-detecting system for an internal combustion engine which has oxygen sensors arranged in the exhaust system, respectively, at locations upstream and downstream of catalytic converters arranged therein, and more particularly to an oxygen sensor deterioration-detecting system for detecting deterioration of the upstream oxygen sensors which are used in carrying out air-fuel ratio control per cylinder group of the engine, such as a V-type engine.

2. Prior Art

In internal combustion engines in general, to control the air-fuel ratio of an air-fuel mixture supplied to the engine to a desired value, an oxygen sensor (hereinafter referred to as "the upstream O2 sensor") is provided in the exhaust system at a location upstream of a catalytic converter arranged therein, for detecting the concentration of oxygen present in exhaust gases, to thereby control the air fuel ratio of the mixture, based on an output from the O2 sensor.

An O2 sensor of this kind is liable to change in characteristics (internal resistance, electromotive force, and response time), due to its heat deterioration or the like. The use of an O2 sensor which has deteriorated characteristics adversely affects the accuracy of the air-fuel ratio control.

To overcome this inconvenience, various proposals have been made, which include a method of additionally providing an O2 sensor in the exhaust system at a location downstream of the catalytic converter (hereinafter referred to as the "downstream O2 sensor"), in order to correct undesirable changes in characteristics of the air-fuel ratio feedback control due to the output from the upstream O2 sensor, whereby the air-fuel ratio feedback control can be carried out with high accuracy. According to this proposal, in controlling the air-fuel ratio of the mixture supplied to the engine to a desired value in a feedback manner responsive to the output from the upstream O2 sensor, a control amount used in the air-fuel ratio feedback control is corrected based on an output from the downstream O2 sensor, to thereby compensate for deviation of the controlled air-fuel ratio from a proper value, due to deterioration of the upstream O2 sensor. However, this proposed method has a disadvantage that when the upstream O2 sensor has become heavily deteriorated beyond the limit of the above-mentioned compensation, it will result in degraded exhaust emission characteristics of the engine.

To overcome this disadvantage, the present assignee has already proposed, e.g. by Japanese Patent Application No. 4-225284, a method which includes controlling the air-fuel ratio of a mixture supplied to an internal combustion engine in a feedback manner responsive to outputs from the upstream and downstream O2 sensors, and then calculating, e.g. a period of inversion of the output from the upstream O2 sensor, to detect deterioration of the upstream O2 sensor, based on the calculated inversion period.

The above proposed method is applied to an engine in which a single O2 sensor is provided in the exhaust system at a location upstream of a catalytic converter arranged therein, and wherein the air-fuel ratio of a mixture supplied to the cylinders is collectively corrected in response to the output from the O2 sensor. On the other hand, there is also known another air-fuel ratio control method, which employs O2 sensors provided for respective cylinder groups and arranged at locations upstream of respective catalytic converters, and wherein air-fuel ratio control amounts are calculated for the respective cylinder groups in a manner independent of the other cylinder groups, to carry out feedback control, based on the calculated control amounts.

The last-mentioned air-fuel ratio control method which controls per cylinder group is superior in air-fuel ratio control accuracy to the aforementioned method, and includes various types, such as a method which controls per bank (right bank and left bank) for a V-type engine, and a method which controls per cylinder group (a first group consisting of #1 and #4 cylinders and a second group consisting of #2 and #3 cylinders) for a straight-type four-cylinder engine.

In the method of controlling per cylinder group, it has been desired to detect deterioration of each of the upstream O2 sensors independently of the other O2 sensors. To meet this desire, an upstream O2 sensor and a downstream O2 sensor may be provided for each cylinder group to detect deterioration of the upstream O2 sensor, which, however, results in a high cost due to an increase in the number of the O2 sensors employed.

SUMMARY OF THE INVENTION

It is the object of the invention to provide an O2 sensor deterioration-detecting system for an internal combustion engine having a plurality of cylinder groups, which is capable of detecting deterioration of upstream O2 sensors provided for respective cylinder groups for use in carrying out air-fuel ratio per cylinder group, at a low cost.

To attain the above object, the present invention provides an oxygen sensor deterioration-detecting system for an internal combustion engine having a plurality of groups of cylinders, an exhaust system having a plurality of exhaust passages extending from respective ones of the groups of cylinders, the exhaust passages having downstream end portions thereof cojoined into a confluent portion, and catalytic exhaust gas-purifying means arranged in the exhaust system, and a plurality of upstream oxygen sensors arranged in respective ones of the exhaust passages at locations upstream of the catalytic exhaust gas-purifying means, comprising:

a single downstream oxygen sensor arranged in the confluent portion of the exhaust passages at a location downstream of the catalytic exhaust gas-purifying means, for detecting a mixed air-fuel ratio of exhaust gases emitted from the groups of cylinders;

a plurality of air-fuel ratio control means responsive to outputs from the upstream oxygen sensors and an output from the downstream oxygen sensor, for determining air-fuel ratio control amounts for respective ones of the groups of cylinders, and for controlling air-fuel ratios of air-fuel mixtures supplied into the respective ones of the groups of cylinders by the use of the air-fuel ratio control amounts determined; and oxygen sensor deterioration-detecting means for detecting deterioration of each of the upstream oxygen sensors, based on an output from the each of the upstream oxygen sensors obtained by operation of a corresponding one of the air-fuel ratio control means.

Preferably, the oxygen sensor deterioration-detecting means detects deterioration of the each of the upstream oxygen sensors, based on an inversion period of the output from the each of the upstream oxygen sensors obtained by the operation of the corresponding one of the air-fuel ratio control means.

For example, the oxygen sensor deterioration-detecting means determines that the each of the upstream oxygen sensors is deteriorated, when the inversion period of the output from the each of the upstream oxygen sensors exceeds a predetermined value.

The oxygen sensor deterioration-detecting system of the invention may be applied to an internal combustion engine wherein the catalytic exhaust gas-purifying means comprises a plurality of catalytic converters arranged in respective ones of the exhaust passages.

Alternatively, the oxygen sensor deterioration-detecting system of the invention may be applied to an internal combustion engine wherein the catalytic exhaust gas-purifying means comprises a single catalytic converter arranged in the confluent portion of the exhaust passages.

According to the oxygen sensor deterioration-detecting system of the invention constructed as above, air-fuel ratio control amounts are calculated for the respective cylinder groups, based on the output from the downstream oxygen sensor and the respective outputs from the upstream oxygen sensors, control the respective air-fuel ratios of mixtures supplied to the respective cylinder groups, based on the respective air-fuel ratio control amounts thus calculated (hereinafter referred to as "the 2-O2 sensor F/B control"). Then, the oxygen sensor deterioration-detecting means detects deterioration of each of the upstream oxygen sensors, based on the output from the downstream oxygen sensor independently of the other upstream oxygen sensor(s). By virtue of the above construction, if the invention is applied to a V-type engine in which cylinders are divided into two cylinder groups of a right bank and a left bank, even when the upstream oxygen sensors arranged at the respective banks are both about to become deteriorated, more specifically, even when an output from the upstream oxygen sensors of one cylinder group (e.g. the right bank) deviates toward the rich side with respect to a stoichiometric air-fuel ratio and an output from the other upstream sensor of the other cylinder group (e.g. the left bank) deviates toward the lean side with respect to the stoichiometric air-fuel ratio, such that the mixed air fuel ratio of exhaust gases emitted from the both banks is equal to the stoichiometric air-fuel ratio ($\lambda=1$), as exemplified in FIG. 10A, the downstream oxygen sensor detects the stoichiometric air-fuel ratio, i.e. it detects an average value of rich and lean air-fuel ratio values detected by the respective upstream oxygen sensors. As a result, correction of the air-fuel ratio control amount based on the output from the downstream oxygen sensor is not made during the 2-O2 sensor F/B control, i.e. the upstream oxygen sensors are not determined to be deteriorated.

Particularly, in an arrangement in which a single catalytic converter is arranged in a confluent exhaust passage portion at which a plurality of exhaust passages extending fro respective cylinder groups cojoin, the catalytic converter causes reaction between unburnt components emitted from one bank and oxygen molecules emitted from another bank, whereby clean exhaust gases are emitted into the atmosphere. Therefore, there is no problem from the viewpoint of exhaust emission characteristics even if neither correction of the air-fuel control amounts nor detection of deterioration of the upstream oxygen sensors is made based on the output from the downstream oxygen sensor in the above-mentioned case.

Further, as shown in FIG. 10B, when an output from the upstream oxygen sensor of one cylinder group (e.g. the right bank) deviates toward the rich side and an output from the other upstream oxygen sensor of the other cylinder group (e.g. the left bank) deviates toward the lean side, and at the same time the deviation toward the lean side is larger in degree than the deviation toward the rich side, the mixed air-fuel ratio of exhaust gases emitted from the both banks becomes lean, whereby the lean mixed air-fuel ratio is detected by the downstream oxygen sensor.

Similarly, when the outputs from the both upstream oxygen sensors deviates toward the rich side (or lean side), the mixed air-fuel ratio of exhaust gases shows a rich (or lean) value, and accordingly the downstream oxygen sensor detects the mixed rich (or lean) air-fuel ratio.

In the latter two cases, correction of the amounts of deviation of the upstream oxygen sensor outputs, i.e. the air-fuel ratio control amounts, is effected based on the output from the downstream oxygen sensor (feedback control), which continues until the downstream oxygen sensor detects the stoichiometric air-fuel ratio ($\lambda=1$). That is, the output from one of the upstream oxygen sensors is corrected toward the rich side and the output from the other upstream oxygen sensor toward the lean side so that the amounts of deviation of the both upstream oxygen sensors become equal to each other, as shown in FIG. 10A.

During the correction based on the downstream oxygen sensor output, deterioration of the upstream oxygen sensors is detected per cylinder group. When deterioration of one of the upstream oxygen sensors occurs to such an extent as exceeds the deterioration degree range within which the air-fuel ratio control amount based on the sensor output can be corrected, an alarm is raised to urge the driver to replace the sensor by a new one to thereby prevent the engine from being operated with degraded exhaust emission characteristics.

As explained above, from the viewpoint of exhaust emission characteristics, there is no problem insofar as clean exhaust gases are emitted into the atmosphere. For example, in FIG. 10A, even if the output from the upstream oxygen sensor of one cylinder group deviates toward the rich side and the output from the oxygen sensor of the other cylinder group toward the lean side, the aforementioned conventional deterioration-detecting method which uses the upstream and downstream oxygen sensors provided per cylinder group executes detection of deterioration of the upstream oxygen sensors, whereas the method according to the present invention regards it unnecessary to carry out the detection of deterioration, when clean exhaust gases are emitted into the atmosphere.

Therefore, according to the arrangement of the invention, deterioration of each of upstream oxygen sensors provided for respective cylinder groups can be made even with a single downstream oxygen sensor during air-fuel ratio control per cylinder group.

The above and other objects, features, and advantages of the invention will become more apparent from the following detailed description taken in conjunction with the accompanying drawings.

BRIEF DESCRIPTION OF THE DRAWINGS

FIG. 6 is a timing chart useful in explaining the operation of the program of FIGS. 5A and 5B;

FIG. 9 is a graph useful in explaining effects of the invention;

FIG. 11 is a fragmentary block diagram showing essential parts of an internal combustion engine to which is applied an oxygen sensor deterioration-detecting system according to a second embodiment of the invention.

DETAILED DESCRIPTION

The invention will now be described in detail with reference to drawings showing embodiments thereof.

Figure 1:
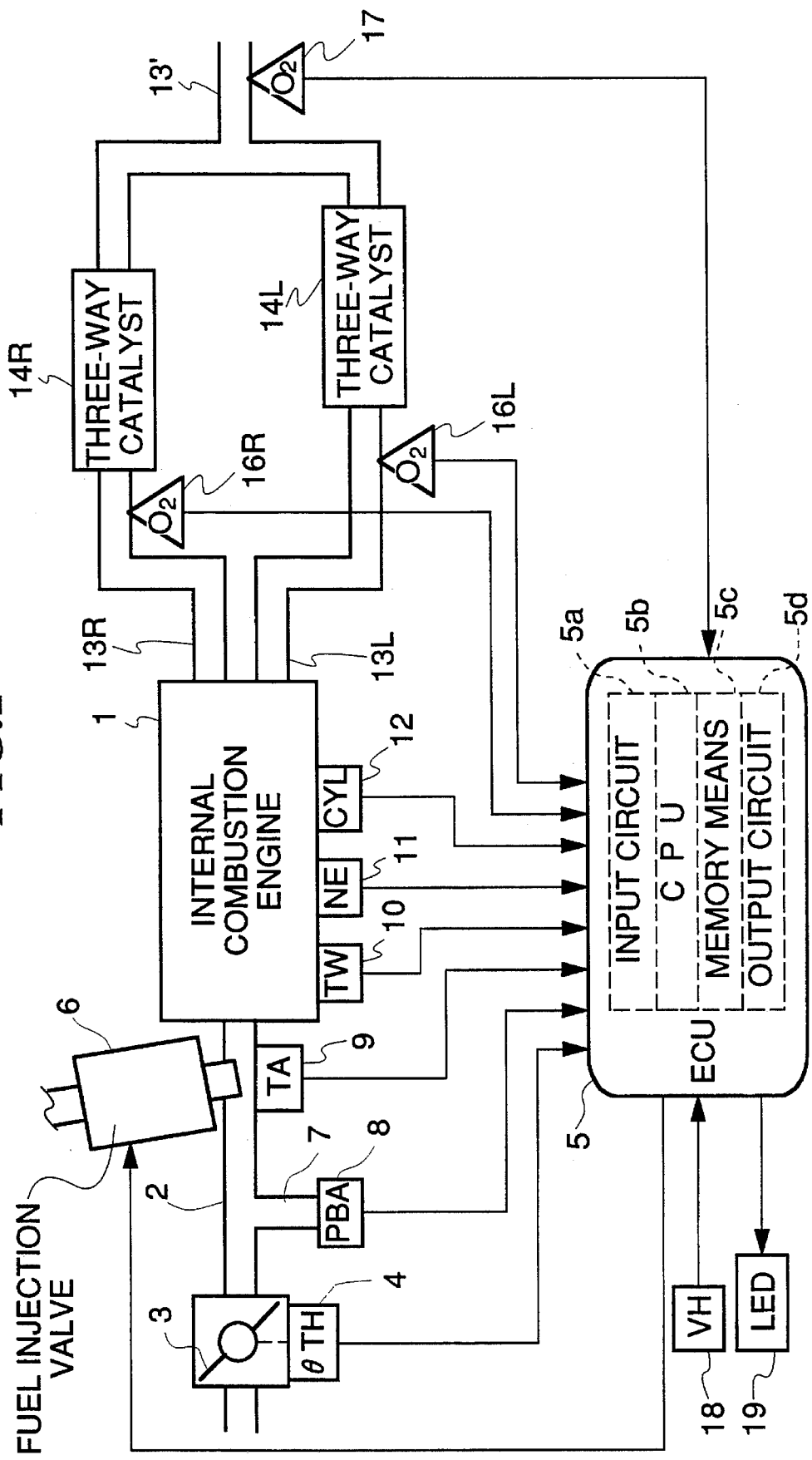
FIG. 1 is a block diagram showing the whole arrangement of an internal combustion engine and an oxygen sensor deterioration-detecting system therefor, according to an embodiment of the invention.

Referring first to FIG. 1, there is shown the whole arrangement of an internal combustion engine and an oxygen sensor deterioration-detecting system therefor, according to an embodiment of the invention. In the FIG., reference numeral 1 designates, for example, a V-type/8-cylinder engine. The engine 1 has two cylinder groups arranged on a right (R) bank and a left (L) bank. Four intake pipes 2, corresponding in number to the number of the cylinders of each bank, extend from respective pairs of cylinders of the two banks. The intake pipes 2 cojoin at an upstream converged portion, in which is arranged a throttle valve 3, to which is connected a throttle valve opening (ΘTH) sensor 4 for generating an electric signal indicative of the sensed throttle valve opening and supplying the same to an electronic control unit (hereinafter referred to as "the ECU") 5.

Fuel injection valves 6 are each provided for each cylinder and arranged in the corresponding intake pipe 2 at a location between the engine 1 and the throttle valve 3 and slightly upstream of an intake valve, not shown. Each fuel injection valve 6 is connected to a fuel pump, not shown, and electrically connected to the ECU 5 to have its valve opening period controlled by a signal therefrom.

On the other hand, an intake pipe absolute pressure (PBA) sensor 8 is connected to the intake pipe 2 via a conduit 7 at a location immediately downstream of the throttle valve 3 for sensing intake pipe absolute pressure (PBA), and is electrically connected to the ECU 5 for supplying an electric signal indicative of the sensed absolute pressure to the ECU 5. An intake air temperature (TA) sensor 9 is inserted into one of the intake pipes 2 at a location downstream of the intake pipe absolute pressure sensor 8 for supplying an electric signal indicative of the sensed intake air temperature TA to the ECU 5.

An engine coolant temperature (TW) sensor 10, which may be formed of a thermistor or the like, is inserted in a coolant-filled cylinder block of the engine for supplying an electric signal indicative of the sensed engine coolant temperature TW to the ECU 5. An engine rotational speed (NE) sensor 11 and a cylinder-discriminating (CYL) sensor 12 are arranged in facing relation to a camshaft or a crankshaft of the engine 1, neither of which is shown. The NE sensor 11 generates a pulse as a TDC signal pulse at one of predetermined crank angles whenever the crankshaft rotates through 180 degrees, while the CYL sensor 12 generates a signal pulse (CRK signal pulse) at a predetermined crank angle of a particular cylinder of the engine, both of the pulses being supplied to the ECU 5.

Three-way catalysts (catalytic converters; hereinafter referred to as "the catalysts") 14R and 14L are arranged, respectively, in exhaust pipes 13R and 13L extending from the respective cylinder groups on the R bank and the L bank of the engine 1, for purifying components, such as HC, CO and NOx in the exhaust gases. Oxygen concentration sensors (hereinafter referred to as "the upstream O2 sensors") 16R and 16L are arranged in the respective exhaust pipes 13R and 13L at locations upstream of the catalysts 14R and 14L. The exhaust pipes 13R and 13L are joined together at a location downstream of the catalysts 14R and 14L, into a confluent exhaust pipe portion 13a. An oxygen concentration sensor (hereinafter referred to as "the downstream O2 sensor") 17 is mounted in the confluent exhaust pipe portion 13a. The O2 sensors 16R, 16L and 17 detect the concentration of oxygen present in the exhaust gases at their respective locations, and generate output signals indicative of the sensed oxygen concentration to the ECU 5. Further, a vehicle speed (VH) sensor 18 is connected to the ECU 5, for detecting the speed VH of an automotive vehicle on which the engine 1 is installed. An LED 19 is connected to the ECU 5 for indicating deterioration of the upstream O2 sensors 16R and 16L.

The ECU 5 comprises an input circuit 5a having the functions of shaping the waveforms of input signals from various sensors as mentioned above, shifting the voltage levels of sensor output signals to a predetermined level, converting analog signals from analog-output sensors to digital signals, and so forth, a central processing unit (hereinafter referred to as "the CPU") 5b, memory means 5c storing various operational programs which are executed in the CPU 5b, and for storing results of calculations therefrom, etc., and an output circuit 5d which supplies driving signals to the fuel injection valves 6.

The CPU 5b operates in response to the above-mentioned engine parameter signals from the sensors to determine operating conditions in which the engine 1 is operating, such as feedback control regions and open-loop control regions, and calculates, based upon the determined engine operating conditions, fuel injection periods R-Tout and L-Tout over which the fuel injection valves 6 for the R and L banks are to be opened, respectively, in synchronism with generation of TDC signal pulses, by the use of the following equation (1):

$$R\text{-}Tout = Ti \times R\text{-}KO2 \times KLS \times K1 + K2$$

$$L\text{-}Tout = Ti \times L\text{-}KO2 \times KLS \times K1 + K2 \qquad (1)$$

where Ti represents a basic fuel injection amount, i.e. a basic value of the fuel injection period Tout, which is determined according to the engine rotational speed NE and the intake pipe absolute pressure PBA. A Ti map for determining the Ti value is stored in the memory means 5c.

R-KO2 represents an air-fuel ratio correction coefficient (hereinafter referred to simply as "the correction coefficient") which is calculated in response to the oxygen concentration in exhaust gases sensed by the O2 sensors 16R and 17. The correction coefficient R-KO2 is set to such a value that the air-fuel ratio of a mixture supplied to the engine becomes equal to a desired value when the engine 1 is operating in the air-fuel ratio feedback control region based on the outputs from the O2 sensors 16R and 17, while it is set to predetermined values corresponding to the respective operating regions of the engine when the engine 1 is in the open-loop control regions. Similarly, L-KO2 represents an air-fuel ratio correction coefficient which is calculated based on the oxygen concentration in exhaust gases sensed by the O2 sensors 16L and 17.

KLS represents a mixture-leaning coefficient, which is set to a predetermined value smaller than 1.0 when the engine 1 is in a predetermined decelerating condition, while it is set to 1.0 when the engine is in a condition other than the predetermined decelerating condition.

K1 and K2 represent other correction coefficients and correction variables, respectively, which are set according to engine operating parameters to such values as optimize engine operating characteristics, such as fuel consumption and engine accelerability.

The CPU 5b supplies driving signals, based on the results thus calculated via the output circuit 5d to the fuel injection valves 6.

The ECU 5 carries out detection of the deterioration of the upstream O2 sensors 16R and 16L in a manner described hereinafter, and energizes the LED 19 as alarming means to be lit up when it detects the deterioration of the O2 sensor 16R or 16L.

Figure 2:
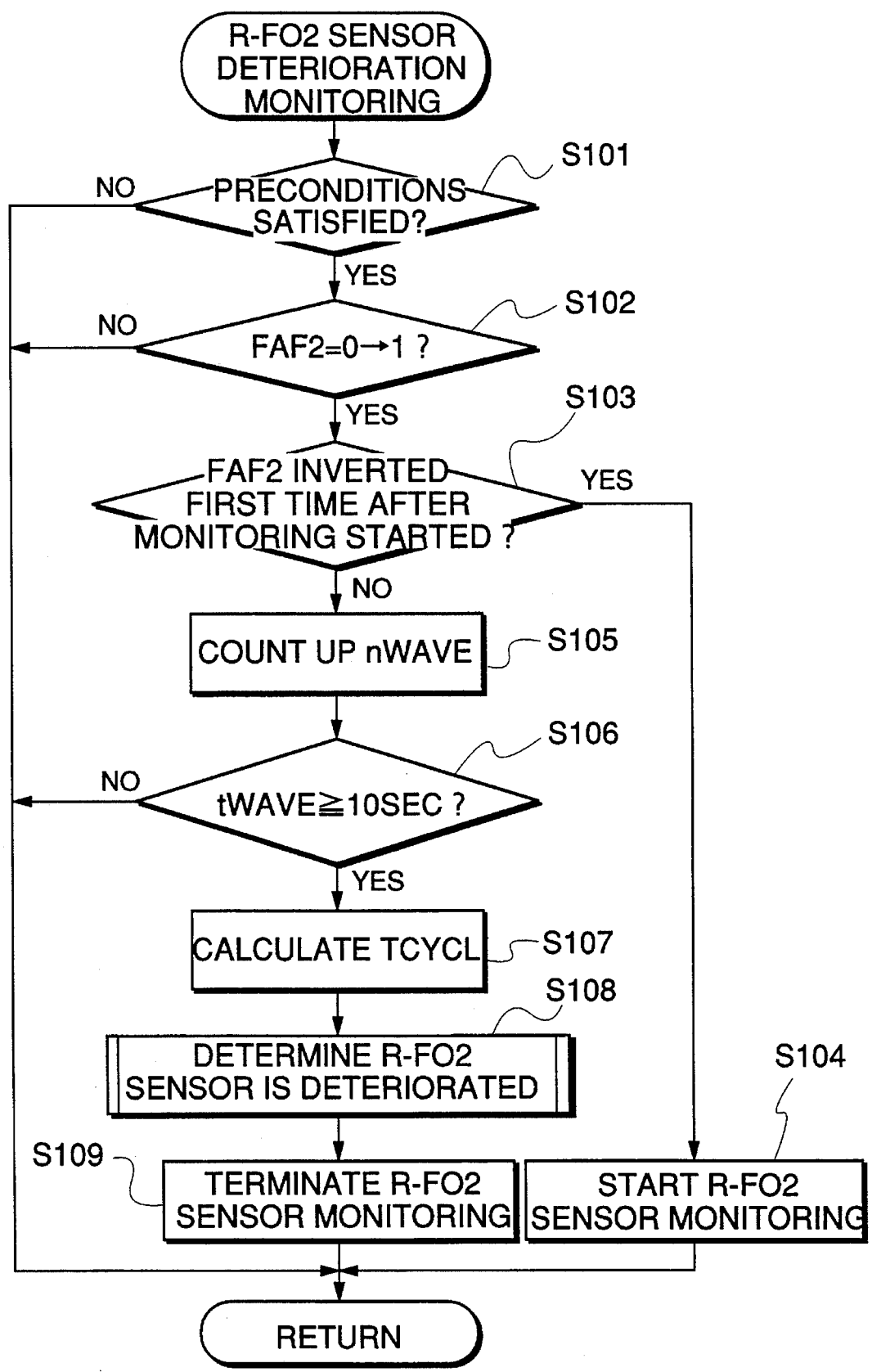
FIG. 2 is a flowchart showing a main routine for detecting deterioration of one of upstream O2 sensors appearing in FIG. 1.

FIG. 2 shows a program (main routine) for executing detection of abnormality (deterioration monitoring) of the upstream O2 sensor 16R arranged in the R bank of the exhaust system.

First, at a step S101, it is determined whether or not monitoring conditions under which the monitoring of deterioration can be carried out are satisfied. If the monitoring conditions are not satisfied, the present routine is immediately terminated, whereas if the monitoring conditions are satisfied, the program proceeds to a step S102.

At the step S102, it is determined whether or not a flag FAF2, referred to hereinafter (see FIG. 5A), has been changed from "0" to "1". If the flag FAF2 remains equal to "0", the present routine is immediately terminated. On the other hand, if the flag FAF2 has been changed from "0" to "1", i.e. if a delay time CDLY1 has elapsed after an output R-FVO2 from the upstream O2 sensor 16R was inverted from a lean value to a rich value, the program proceeds to a step S103, where it is determined whether or not an inversion of the output from the upstream O2 sensor 16R has first taken place after the present monitoring of the O2 sensor 16R was permitted. If this determination is carried out for the first time, it is the first inversion after the monitoring of the upstream O2 sensor 16R was permitted, so that the answer to the question is affirmative (YES), and then the program proceeds to a step S104, where the monitoring of the upstream O2 sensor 16R is started, followed by terminating the program.

When the second and subsequent inversions of the O2 sensor output take place after the monitoring of the upstream O2 sensor 16R was permitted, the answer to the question of the step S103 becomes negative (NO), and then the program proceeds to a step S105, where the number of times of inversions nWAVE is counted up, i.e. the number of times nWAVE is increased by an increment of 1 whenever an inversion takes place, and then at a step S106, it is determined whether or not a time period tWAVE measured after the monitoring was started exceeds a predetermined value (e.g. 10 sec.). If the answer to this question is negative (NO), the present routine is immediately terminated, whereas if the answer is affirmative (YES), the program proceeds to a step S107, where an inversion period TCYCL is calculated by the use of the following equation (2):

$$TCYCL = TWAVE/nWAVE \qquad (2)$$

In this connection, a counter (upcounter) which counts the time period tWAVE is reset to "0" and started when the monitoring is started at the step S104. Similarly, a counter (upcounter) which counts the number of times nWAVE is reset and started at the step S104.

After the inversion period TCYCL is calculated at the step S107, a deterioration determination, described in detail hereinafter, is carried out at a step S108 to determine whether or not the upstream O2 sensor 16R is deteriorated. The results of the determination are stored into the memory means 5c, followed by terminating the program.

Figure 3:
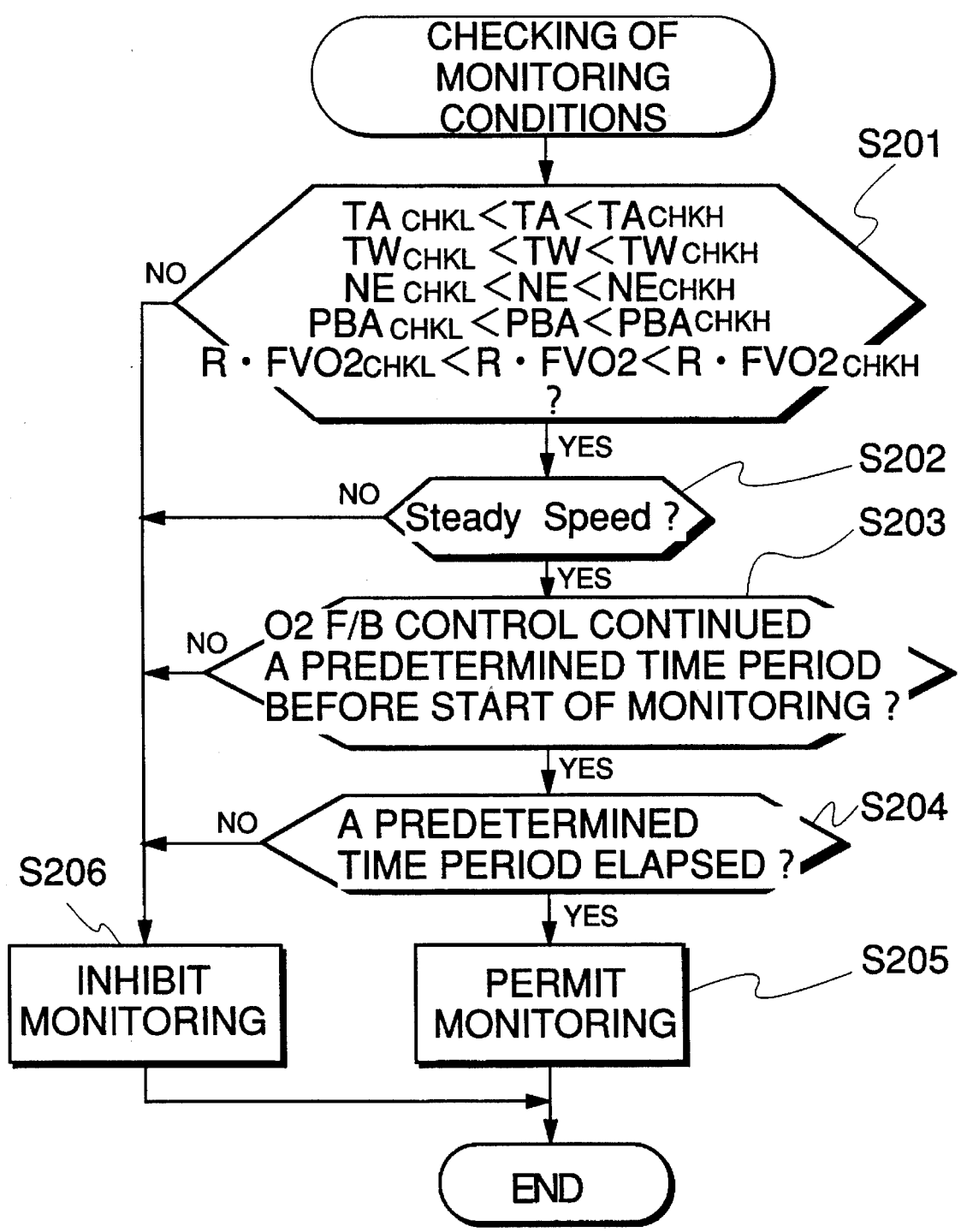
FIG. 3 is a flowchart showing a subroutine for determining whether or not monitoring conditions are satisfied for starting the monitoring of deterioration of the upstream O2 sensor.

FIG. 3 shows a subroutine for determining whether or not the monitoring conditions are satisfied, which is executed at the step S101 of the FIG. 2 program. First, at a step S201, operating conditions of the engine 1 are determined. More specifically, it is determined whether or not an output TA from the intake air temperature sensor 9 falls within a predetermined range of TACHKL to TACHKH (e.g. 60° C. to 100° C.), whether or not an output TW from the engine coolant temperature sensor 10 falls within a predetermined range of TWCHKL to TWCHKH (e.g. 60° C. to 100° C.), whether or not an output NE from the engine rotational speed sensor 11 falls within a predetermined range of NECHKL to NECHKH (e.g. 2800 rpm to 3200 rpm), whether or not an output PBA from the intake pipe absolute pressure sensor 8 falls within a predetermined range of PBACHKL to PBACHKH (e.g. −350 mmHg to −250 mmHg), and whether or not the output R-FVO2 from the upstream O2 sensor 16R falls within a predetermined range of R-FVO2CHKL to R-FVO2CHKH. Then, it is determined at a step S202 whether or not the vehicle speed VH is steady, i.e. whether or not the output VH from the vehicle speed sensor 18 has continued to be within a variation range of 0.8 km/sec over a predetermined time period (e.g. 2 sec). Then, it is determined at a step S203 whether or not the air-fuel ratio feedback control has been carried out over a predetermined time period (e.g 10 sec) before the monitoring was permitted at the step S203. Further, it is determined at a step S204 whether or not all the above conditions have continued to be satisfied over a predetermined time period (e.g. 2 sec).

Then, if the answers to the questions of the above steps S201 to S204 are all affirmative (YES), the monitoring of the upstream O2 sensor 16R is permitted at a step S205, and then the program proceeds to the step S102 in FIG. 2, whereas if any of the steps is negative (NO), the monitoring is inhibited at a step S206, followed by terminating the main routine of FIG. 2.

Figure 4:
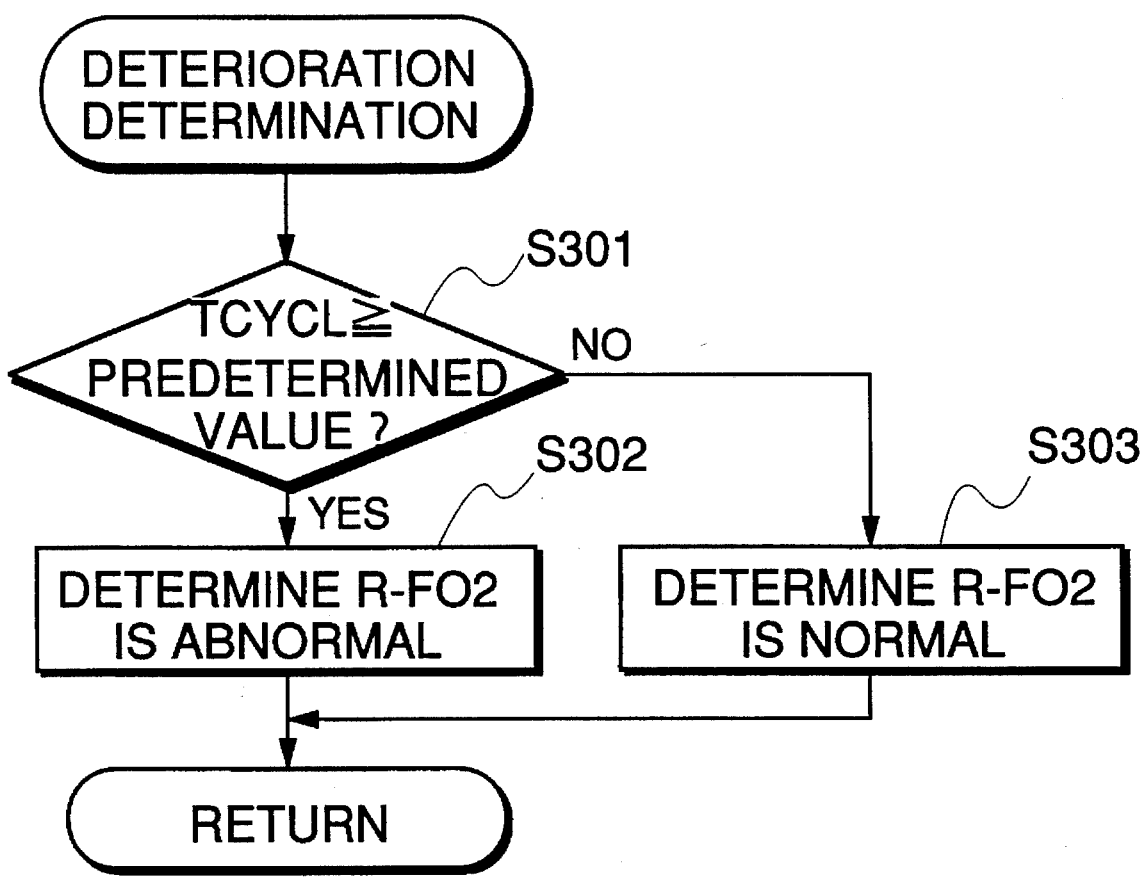
FIG. 4 is a flowchart showing a subroutine for executing determination of O2 sensor deterioration at a step of the FIG. 2 main routine.

FIG. 4 shows a subroutine for carrying out the determination of deterioration of the upstream O2 sensor 16R, which is executed at the step S108 of the FIG. 2 main routine.

First, at a step S301, it is determined whether or not the inversion period TCYCL calculated at the step S107 of the FIG. 2 program exceeds a predetermined value (which is set to a value corresponding to 1.5 times as large as a standard level which can be assumed when the sensor functions normally). If the answer to the question is affirmative (YES), it is determined at a step S302 that the upstream O2 sensor 16R is abnormal, and at the same time the LED 19 is lit up to alert the driver, followed by terminating the routine. If the answer to the question at the step S301 is negative (NO), i.e. if the inversion period TCYCL is below the predetermined value, the program proceeds to a step S303, where it is determined that the upstream O2 sensor 16R is normal, followed by terminating the routine. In this connection, the predetermined value may be set to proper values depending on operating conditions of the engine, to further improve the accuracy of abnormality detection.

In this way, the monitoring of the upstream O2 sensor 16R is executed. The monitoring of the upstream O2 sensor 16L is executed in the same manner as described above. More specifically, in the monitoring of deterioration of the upstream O2 sensor 16R described by the use of the programs of FIGS. 2 to 4, the O2 sensor 16R and the output R-FVO2 are replaced by the O2 sensor 16L and the output L-FVO2, respectively. Next, description will be made as to air-fuel ratio feedback control using one of the upstream O2 sensor 16R and 16L and the downstream O2 sensor 17 (hereinafter referred to as "the 2-O2 sensor F/B control").

Figure 5A:
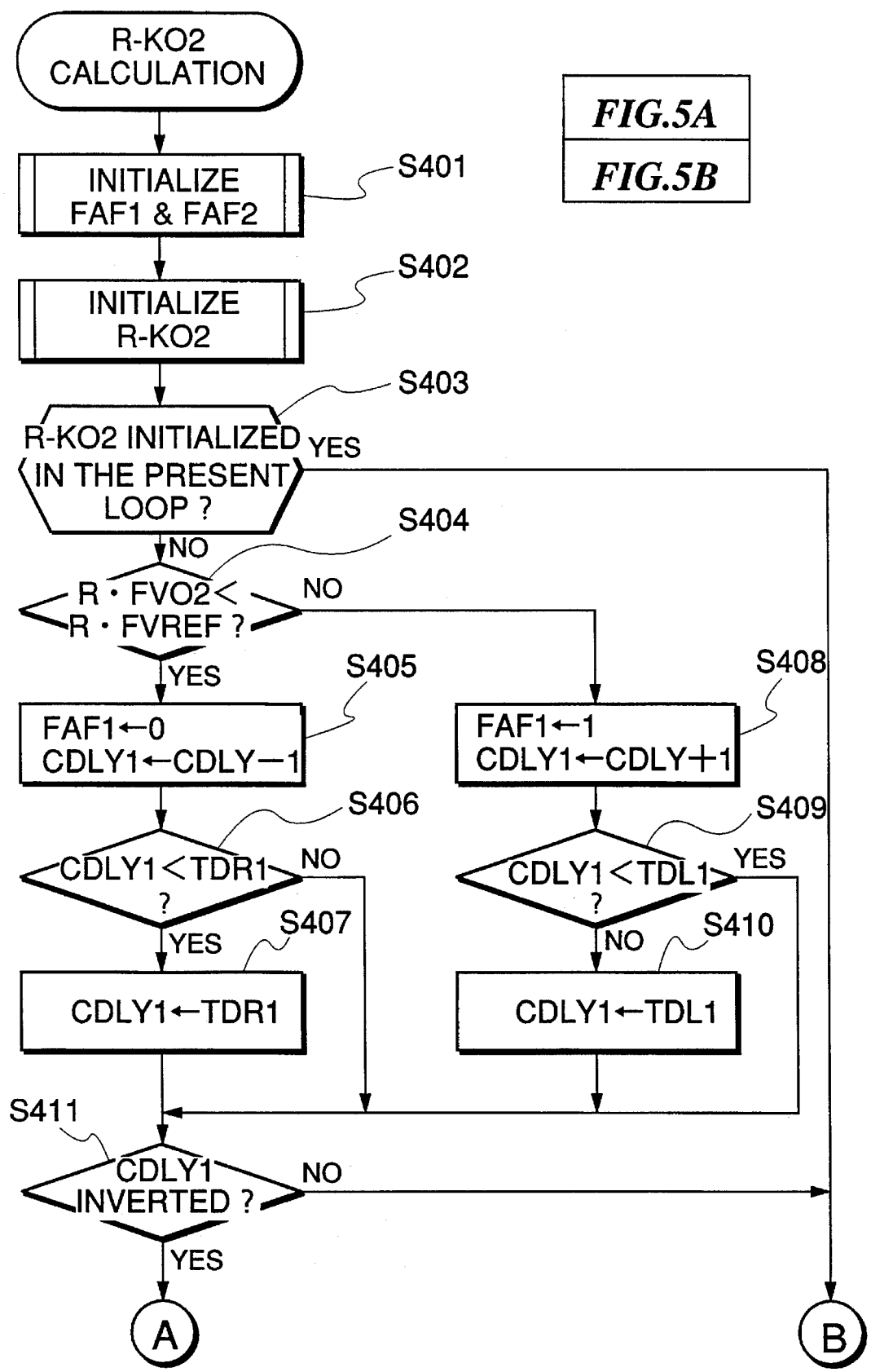
FIG. 5A is a flowchart showing a routine for calculating an air-fuel ratio correction coefficient R-KO2 for a right bank applied in air-fuel ratio feedback control carried out by the use of two O2 sensors.
Figure 5B:
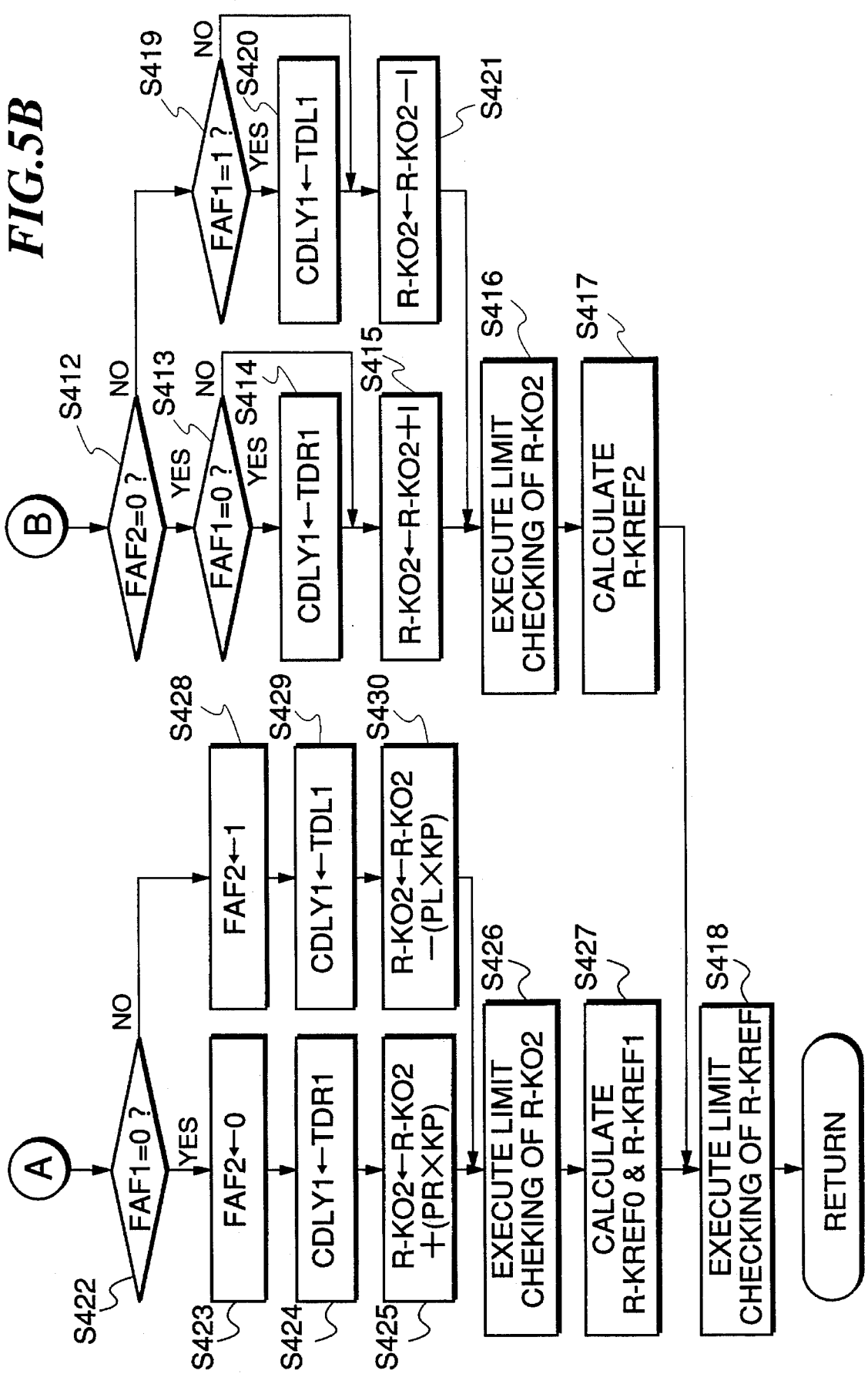
FIG. 5B is a continued part from the FIG. 5A flowchart.

FIG. 5A and FIG. 5B show a subroutine for calculating the air-fuel ratio correction coefficient R-KO2 applied during the 2-O2 sensor F/B control. According to this program, the air-fuel ratio correction coefficient R-KO2 is calculated based on the output R-FVO2 from the upstream O2 sensor 16R and an output RVO2 from the downstream O2 sensor 17 such that the air-fuel ratio of the air-fuel mixture supplied to the engine becomes equal to a stoichiometric value ($\lambda = 1$).

First, at a step S401, flags FAF1 and FAF2 are initialized. The flag FAF1 indicates lean and rich states of the output R-FVO2 from the upstream O2 sensor 16R, when set to "0" and "1", respectively, and the flag FAF2 indicates lean and rich states of the same after a predetermined delay time has been counted up by a counter CDLY1, referred to hereinafter, when set to "0" and "1", respectively. Then, at a step S402, the air-fuel ratio correction coefficient R-KO2 is initialized (e.g. set to an average value R-KREF thereof), followed by the program proceeding to a step S403.

At the step S403, it is determined whether or not the air-fuel ratio correction coefficient R-KO2 has just been initialized in the present loop. If the answer to this question is negative (NO), the program proceeds to a step S404, where it is determined whether or not the upstream O2 sensor output R-FVO2 is lower than a reference value R-FVREF (threshold value for determining whether the output R-FVO2 is rich or lean). If the answer to this question is affirmative (YES), i.e. if R-FVO2<R-FVREF, it is determined that the output R-FVO2 shows a lean value, and then the flag FAF1 is set to "0" at a step S405, and at the same time the count value CDLY of the counter CDLY1 (set value: CDLY1) for counting a P-term generation delay time TDR1 is decreased by a decrement of 1 (see T4 and T10 of FIG. 6(c)). More specifically, if R-FVO2<R-FVREF, the flag FAF1 is set to "0" and the count value CDLY of the counter CDLY1 is decreased by a decrement of 1 to thereby obtain the set value CDLY1 whenever the present step is carried out. Then, at a step S406, it is determined whether or not the set value CDLY1 is smaller than a predetermined delay time TDR1. If the answer to this question is affirmative (YES), i.e. if CDLY1<TDR1, the set value CDLY1 is reset to the delay time TDR1 at a step S407.

On the other hand, if the answer to the question of the step S404 is negative (NO), i.e. if R-FVO2≧R-FVREF, which means that the output R-FVO2 shows a rich value, the flag FAF1 is set to "1", and at the same time the count value CDLY is increased by an increment of 1 at a step S408 (see T2, T6 and T8 of FIG. 6(c)). More specifically, if R-FVO2≧R-FVREF, the flag FAF1 is set to "1" and the count value CDLY of the counter CDLY1 is increased by an increment of 1 to thereby obtain the set value CDLY1 whenever the present step is carried out. Then, at a step S409, it is determined whether or not the set value CDLY1 is smaller than a predetermined delay time TDL1. If the answer to this question is negative (NO), i.e. if CDLY1≧TDL1, the set value CDLY1 is reset to the delay time TDL1 at a step S410.

If the answer to the question at the step S406 is negative (NO), i.e. if CDLY1≧TDR1, the program skips over the step S407 to a step S411. Similarly, if the answer to the question at the step S409 is affirmative (YES), i.e. if CDLY1≧TDL1, the program skips over the step S410 to the step S411.

At the step S411, it is determined whether or not the sign of the count value CDLY1 has been inverted. That is, it is determined whether or not the delay time TDR1 or TDL1 has been counted up after the output R-FVO2 from the upstream O2 sensor 16R crossed the reference value R-FVREF. If the answer to this question is negative (NO), i.e. if the delay time TDR1 or TDL1 has not elapsed, the program proceeds to a step S412, where it is determined whether or not the flag FAF2 has been set to "0". If the answer to this question is affirmative (YES), it is determined at a step S413 whether or not the flag FAF1 has been set to "0". If the answer to this question is affirmative (YES), it is judged that the air-fuel ratio has continuously been lean, so that the program proceeds to a step S414, where the set value CDLY1 is reset to the delay time TDR1, followed by the program proceeding to a step S415. If the answer to the question at the step S413 is negative (NO), it is judged that the delay time period has not elapsed yet after the output R-FVO2 from the upstream O2 sensor 16R was inverted from a lean side to a rich side, i.e. after it crossed the reference value R-FVREF, so that the program skips over the step S414 to the step S415.

At the step S415, a present value of the air-fuel ratio correction coefficient R-KO2 is obtained by adding the integral term I to a value of the coefficient R-KO2 calculated in the immediately preceding loop, by the use of the following equation (3):

$$R\text{-}KO2 = R\text{-}KO2 + I \tag{3}$$

After execution of the step S415, limit checking of the resulting value of the correction coefficient R-KO2 is performed by a known method at a step S416, calculation of a value R-KREF2 (learned value of the correction coefficient R-KO2 used in starting the vehicle) at a step S417, and limit checking of the resulting value R-KREF2 at a step S418, followed by terminating the program.

On the other hand, if the answer to the question of the step S412 is negative (NO), i.e. if the flag FAF2 is equal to "1", it is further determined at a step S419 whether or not the flag FAF1 is equal to "1". If the answer to this question is affirmative (YES), it is judged that the air-fuel ratio has continuously been rich, and then at a step S420, the set value CDLY1 is reset to the delay time TDL1 again, followed by the program proceeding to a step S421. On the other hand, if the answer to the question of the step S419 is negative (NO), it is judged that the delay time period has not elapsed yet after the output R-FVO2 from the upstream O2 sensor 16R was inverted from the rich side to the lean side, so that the program skips over the step S420 to a step S421. At the step S421, the present value of the correction coefficient R-KO2 is calculated by subtracting the integral term I from the immediately preceding value of the correction coefficient R-KO2 by the use of the following equation (4):

$$R\text{-}KO2 = R\text{-}KO2 - I \quad (4)$$

Then, the above steps S416 to S418 are carried out, followed by terminating the routine.

In this way, when the sign of the set value CDLY1 has not been inverted, the statuses of the flags FAF1 and FAF2 are checked to determine whether or not the output R-FVO2 from the upstream O2 sensor 16R has been inverted from the lean side to the rich side or vice versa, and the correction coefficient R-KO2 is calculated based on results of the check.

On the other hand, if the answer to the question of the step S411 is affirmative (YES), i.e. if the sign of the count value of the counter CDLY1 has been inverted, that is, if the delay time TDR1 or the delay time TDL1 has elapsed after the output R-FVO2 from the upstream O2 sensor 16R was inverted from the lean side to the rich side or vice versa, the program proceeds to a step S422, where it is determined whether or not the flag FAF1 is equal to "0", i.e. whether or not the output R-FVO2 from the upstream O2 sensor 16R shows a lean value. If the answer to the question at the step S422 is affirmative (YES), i.e. if FAF1=0 (the output R-FVO2 shows a lean value), the program proceeds to a step S423, where the flag FAF2 is set to "0", and then at a step S424, the set value CDLY1 is reset to the delay time TDR1, followed by the program proceeding to a step S425.

At the step S425, the present value of correction coefficient R-KO2 is calculated by adding the product of a proportional term PR and a coefficient KP to the immediately preceding value of correction coefficient R-KO2 by the use of the following equation (5):

$$R\text{-}KO2 = R\text{-}KO2 + (PR \times KP) \quad (5)$$

where R-KO2 on the right side represents the immediately preceding value of the correction coefficient R-KO2, and the proportional term PR is a correction term employed for shifting the air-fuel ratio toward the rich side by increasing the correction coefficient R-KO2 in a stepwise manner when the delay time TDL1 has elapsed after the output R-FVO2 from the upstream O2 sensor 16R was inverted from the rich side to the lean side with respect to the stoichiometric value. The proportional term PR is varied according to the output RVO2 from the downstream O2 sensor 17, as described hereinafter. The coefficient KP is set in response to the operating condition of the engine 1.

Then, limit checking of the correction coefficient R-KO2 calculated as above is carried out at a step S426, and a value R-KREF0 (average value of the correction coefficient R-KO2 calculated during idling of the engine) and a value R-KREF1 (average value of the correction coefficient R-KO2 calculated when the engine is not idling) are calculated at a step S427. Then, the program proceeds to the step S418, followed by terminating the program.

If the answer to the question of the step S422 is negative (NO), i.e. if the output R-FVO2 from the upstream O2 sensor 16R shows a rich value (FAF1=1), the program proceeds to a step S428, where the flag FAF2 is set to "1", and then at a step S429, the set value CDLY1 is reset to the delay time TDL1, followed by the program proceeding to a step S430.

At the step S430, the present value of the correction coefficient R-KO2 is calculated by subtracting the product of a proportional term PL and the coefficient KP from the immediately preceding value of the correction coefficient R-KO2 by the use of the following equation (6):

$$R\text{-}KO2 = R\text{-}KO2 - (PL \times KP) \quad (6)$$

where R-KO2 on the right side represents the immediately preceding value of the correction coefficient R-KO2, and the proportional term PL is a correction term employed for shifting the air-fuel ratio toward the lean side by decreasing the correction coefficient KO2 in a stepwise manner when the delay time TDR1 has elapsed after the output R-FVO2 from the upstream O2 sensor 16R was inverted from the lean side to the rich side with respect to the stoichiometric value. The proportional term PL is varied according to the output RVO2 from the downstream O2 sensor 17, as described hereinafter.

Then, the steps S426, S427 and S418 are sequentially carried out, followed by terminating the program. In this way, the timing of generation of the integral term I and the proportional term PR or PL of the correction coefficient R-KO2 is calculated based on the output R-FVO2 from the upstream O2 sensor 16R. Further, when the air-fuel ratio feedback control is started, at the step S402 in FIG. 5A, the learned value R-KREF is set as an initial value of the correction coefficient R-KO2, and then the program proceeds to the step S403. Then, the answer to the question of the step S403 is affirmative (YES), so that the program proceeds therefrom to the steps S412 to S421 to calculate the correction coefficient R-KO2, followed by terminating the program.

The air-fuel ratio correction coefficient L-KO2 for controlling the air-fuel ratio of a mixture supplied into the cylinders on the L bank may also be calculated similarly to the calculation of the R-KO2 value described hereinabove, i.e. by a program similar to the program of FIGS. 5A and 5B, in which the coefficient R-KO2 is replaced by the coefficient L-KO2.

Figure 7:
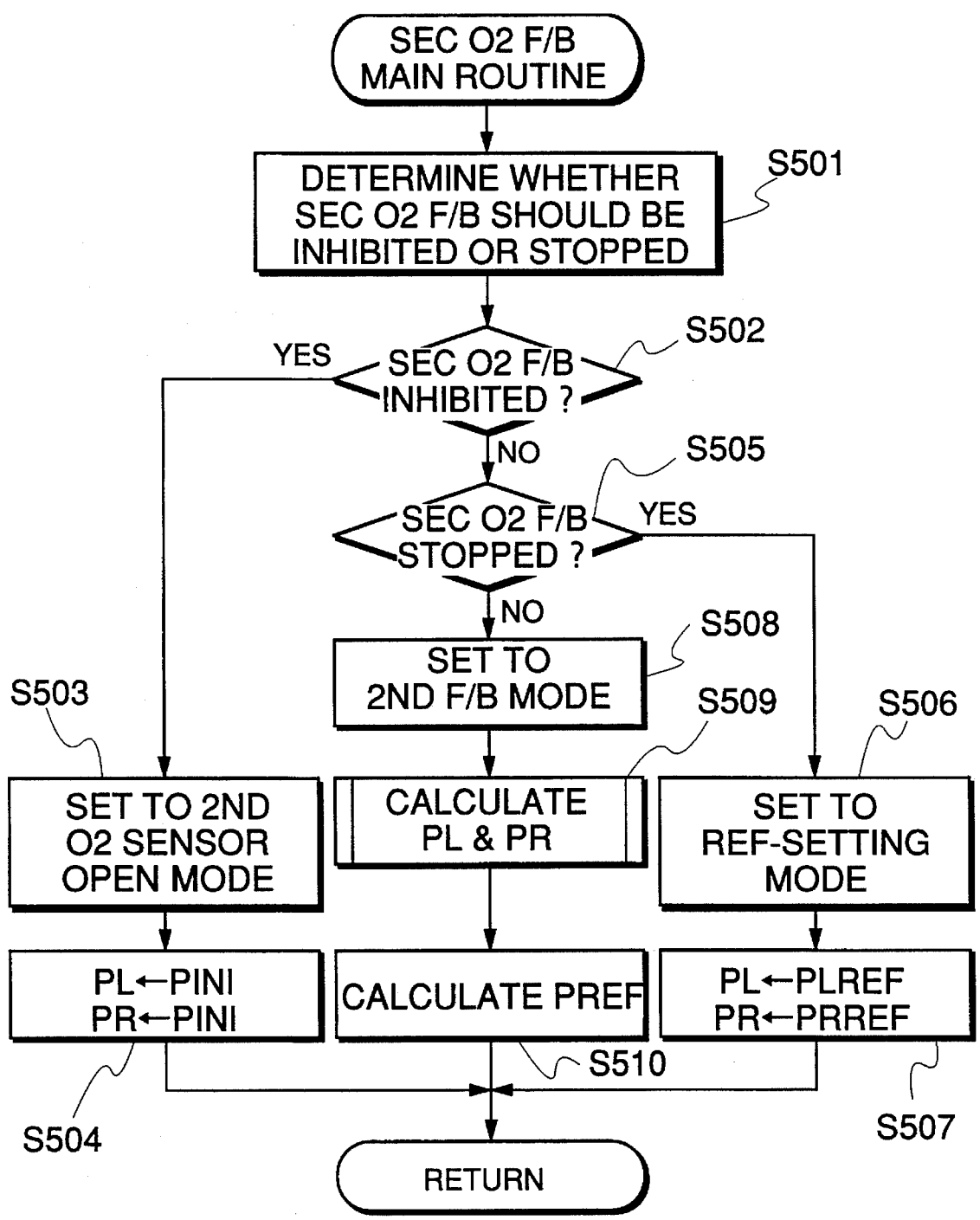
FIG. 7 is a flowchart showing a main routine for executing air-fuel ratio feedback control based on an output from a downstream O2 sensor.

FIG. 7 shows a main routine for carrying out the air-fuel ratio feedback control, based on the output from the downstream O2 sensor 17. This program is for correcting a deviation in the control amount (R-KO2 or L-KO2) based on the the output R-FVO2 or L-FVO2 from the respective upstream O2 sensor 16R or 16L in response to the output RVO2 from the downstream O2 sensor 17.

First, at a step S501, a feedback control execution-determining processing is carried out for determining whether the air-fuel ratio feedback control (hereinafter referred to as "the secondary O2 sensor F/B control") based on the output RVO2 from the downstream O2 sensor 17 should be inhibited or temporarily stopped. The secondary O2 sensor F/B control is inhibited when disconnection/short-circuit of the downstream O2 sensor 17 is detected, when the air-fuel ratio feedback control based on the upstream O2 sensor 16R or 16L is not being executed, or when the engine is idling, etc. The secondary O2 sensor F/B control is temporarily stopped when the downstream O2 sensor 17 has not been activated, when the output RFVO2 from the downstream O2 sensor 17 is in a transient state, when a predetermined time period has not elapsed after inhibition of the secondary O2 sensor F/B control, or when a predetermined time period has not elapsed after temporary stoppage of the same.

Then, at a step S502, it is determined whether or not the secondary O2 sensor F/B control is being inhibited. If the answer to the question is affirmative (YES), the program proceeds to a step S503, where the air-fuel ratio control is set to a downstream O2 sensor-open mode, and then the proportional terms PL and PR are both set to an initial value PINI of the proportional term at a step S504, followed by terminating the program.

If the answer to the question of the step S502 is negative (NO), it is determined at a step S505 whether or not the secondary O2 sensor F/B control is being temporarily stopped. If the answer to this question is affirmative (YES), the air-fuel ratio control is set to a REF-setting mode at a step S506, and then at a step S507 the proportional terms PL and PR are set to respective learned values PLREF and PRREF calculated by a PREF calculation processing, described hereinafter.

If the answer to the question of the step S505 is negative (NO), the air-fuel ratio control is set to a secondary O2 sensor F/B mode at a step S508, and at a step S509 the proportional terms PL and PR are calculated by a subroutine, described hereinafter. Further, the PREF-calculation processing is carried out at a step S510, followed by terminating the program.

Figure 8:
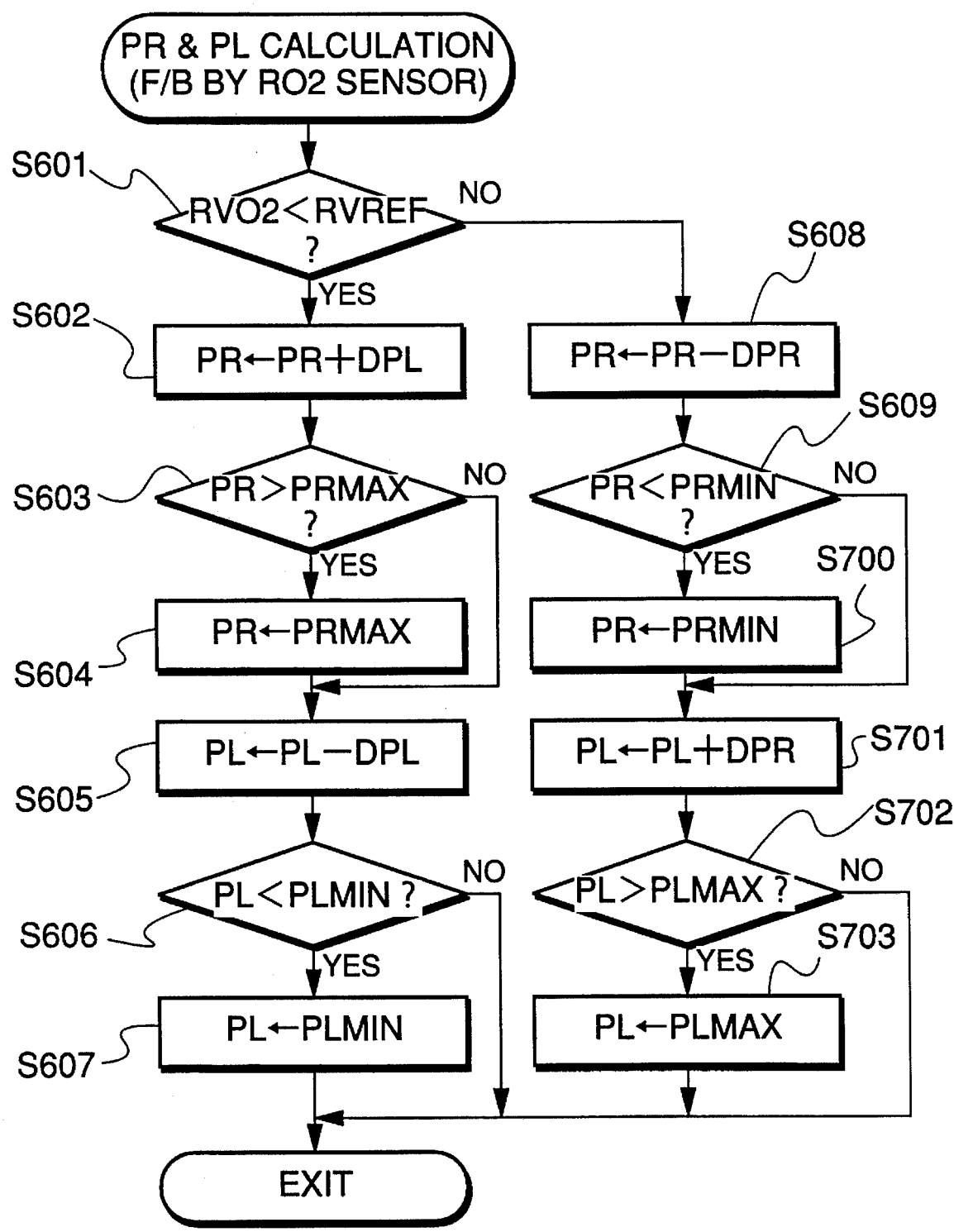
FIG. 8 is a flowchart showing a subroutine for calculating parameter values PR and PL, based on the output from the downstream O2 sensor.

FIG. 8 shows a program for calculating the proportional terms PL and PR executed at the step S509 in FIG. 7. In the present program, the PL and PR terms are calculated in response to a variation in the output RVO2 from the downstream O2 sensor 17.

The PR and PL values are basically calculated based on the output voltage RVO2 from the downstream O2 sensor 17 during execution of the secondary O2 sensor F/B control by the downstream O2 sensor 17. However, when the secondary O2 sensor F/B control cannot be executed (e.g. during idling of the engine, when the downstream O2 sensor 17 is inactive, etc.), predetermined values or the learned values calculated during the feedback control are applied as the PR and PL values.

At a step S601, it is determined whether or not the downstream O2 sensor output voltage RVO2 is lower than a reference value RVREF (e.g. 0.45 V). If RVO2< RVREF, the program proceeds to a step S602, where a correction term DPL applied when the air-fuel ratio is determined to be lean is added to the PR value. If the PR value after the addition exceeds an upper limit value PRMAX at a step S603, the PR value is set to the upper limit value PRMAX at a step S604.

At the next step S605, the correction term DPL is subtracted from the PL value. If the PL value after the subtraction is smaller than a lower limit value PLMIN at a step S606, the PL value is set to the lower limit value PLMIN at a step S607.

On the other hand, if the answer to the question of the step S601 is negative (NO), i.e. if RVO2≧ RVREF, the program proceeds to a step S608, where a correction term DPR applied when the air-fuel ratio is determined to be rich is subtracted from the PR value. If it is determined at a step S609 that the PR value after the subtraction is smaller than a lower limit value PRMIN, the PR value is set to the lower limit value PRMIN at a step S700.

Then, at a step S701, the correction term DPR is added to the PL value. If it is determined at a step S702 that the PL value after the addition is larger than an upper limit value PLMAX, the PL value is set to the upper limit value PLMAX at a step S703.

According to the program of FIG. 8, during a time period over which RVO2<RVREF holds, the PR value is increased within a range between the lower and upper limit values PRMIN and PRMAX, while the PL value is decreased within a range between the lower and upper limit values PLMIN and PLMAX. On the other hand, during a time period over which RVO2≧RVREF holds, the PR value is decreased and the PL value is increased within the above-mentioned respective ranges.

As described above, according to the present embodiment, the PL term and the PR term which represent feedback constants are calculated based on the output from the downstream O2 sensor 17. Then, the R-KO2 value and the L-KO2 value are independently calculated in response to the outputs from the respective upstream O2 sensors 16R and 16L, by the use of the thus calculated PL term and PR term, to thereby carry out the air-fuel ratio feedback control. At the same time, deterioration of each of the upstream O2 sensors 16R and 16L is detected based on the inversion period of the output therefrom.

Figure 10A:
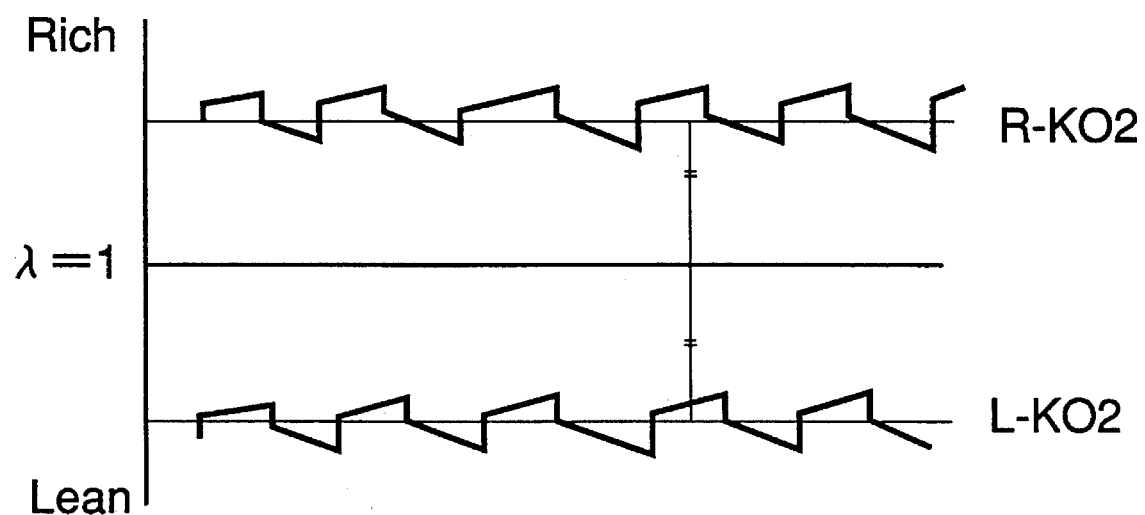
FIGS. 10A and 10B are timing charts useful in explaining the operation of the invention.
Figure 10B:
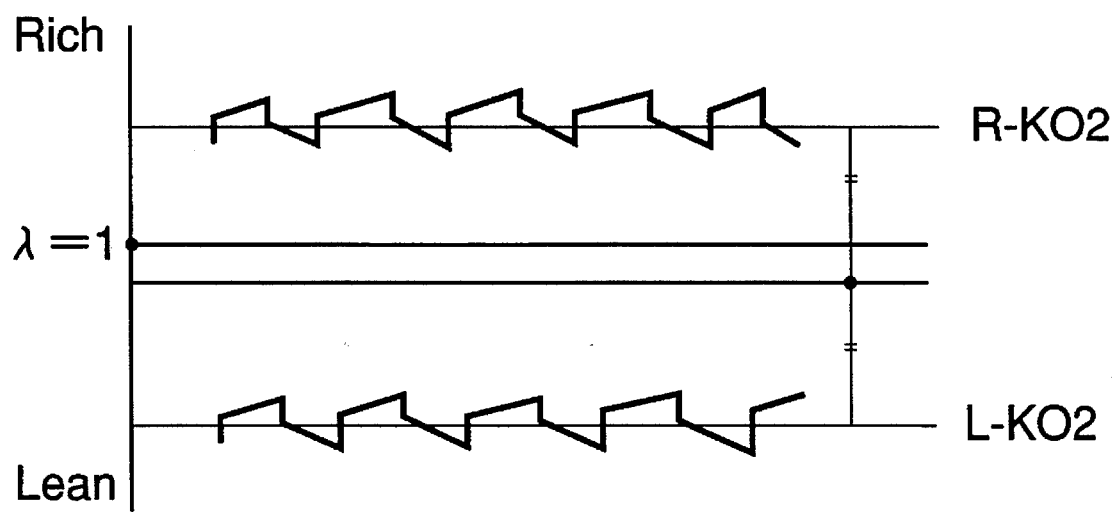

During the above second F/B control, the downstream O2 sensor 17 detects the mixed air-fuel ratio of exhaust gases emitted from the both banks. When the upstream O2 sensor 16R and 16L are deteriorated so that their output deviate toward the rich and lean sides as illustrated in FIG. 10A, if the mixed air-fuel ratio of exhaust gases are equal to the stoichiometric value, correction of the R-KO2 and L-KO2 values by the secondary O2 sensor F/B control is not effected. This is because, when the mixed air-fuel ratio is equal to the stoichiometric value, exhaust gases emitted to the atmosphere is clean, and therefore there is no problem from the viewpoint of exhaust emission characteristics even if the correction of the R-KO2 and L-KO2 values by the secondary O2 sensor F/B control is not effected. Thus, the use of the single downstream O2 sensor in the air-fuel ratio control per cylinder group provides the following advantages:

That is, according to the arrangement of the invention, as mentioned above, the frequency at which correction of the KO2 value is effected based on the output from the downstream O2 sensor during the 2-O2 sensor F/B control is lower than the frequency by the conventional 2-O2 sensor F/B control which employs downstream O2 sensors for the respective cylinder groups, and therefore the frequency 1/TCYL' of the R-KO2 and/or L-KO2 value (TCYL'= inversion period (see FIG. 6)), is not lowered, leading to improved purifying performance of the catalytic converters provided for the respective banks. More specifically, in the conventional 2-O2 sensor F/B control, the frequency of the KO2 value 1/TCYL' is lowered as a result that the controlled air-fuel ratio is converged to the stoichiometric value by the output from the downstream O2 sensor. That is, when one of the upstream O2 sensors is deteriorated, the KO2 value based on the upstream O2 sensor is corrected toward the rich side or toward the lean side with respect to the stoichiometric air-fuel ratio, so that the KO2 value has a waveform with a longer rich period and a longer lean period, i.e. the frequency 1/TCYL' of the KO2 value lowers. Accordingly, the maximum and minimum values of the KO2 waveform largely deviate from a center value thereof (stoichiometric air-fuel ratio). When the deterioration of the upstream O2 sensor further advances, the amount of the deviation further increases, so that the amounts of CO and HC components of exhaust gases generated when the air-fuel ratio assumes a rich value and NOx component of the same generated when the air-fuel ratio assumes a lean value become too large to be processed or purified by the catalytic converters, i.e. the air-fuel ratios of exhaust gases fall out of the windows of the catalytic converters and the O2 amounts stored in the catalytic converters are used up, resulting in degraded exhaust emission characteristics. Sometimes, surging is generated by vibration of the KO2 value with a decreased frequency. Therefore, in the conventional 2-O2 sensor F/B control, it is determined that the upstream O2 sensor is deteriorated when the amounts of CO and HC or the amount of NOx exceeds a value corresponding to 1.5 times as large as a standard level which can be assumed when the upstream O2 sensor functions normally, to urge the driver to replace the O2 sensor by a fresh one.

On the other hand, in the 2-O2 sensor F/B control according to the present invention which employs the single downstream O2 sensor for all the cylinder groups, as described hereinabove, when the controlled air-fuel ratios on the right and left bank sides deviate with respect to the stoichiometric air-fuel ratio to the same degree and in the opposite directions, the mixed air-fuel ratio of exhaust gases from the both banks becomes substantially equal to the stoichiometric air-fuel ratio, and accordingly correction by the 2-O2 sensor F/B control is not effected. Therefore, the frequencies of the KO2 values are not decreased, to thereby prevent exhaust emission characteristics from being degraded. Then, the inversion periods of the outputs from the respective upstream O2 sensor (equivalent to the inversion period of the KO2 value) are short, so that the upstream O2 sensors are not determined to be deteriorated.

Thus, according to the present invention, the upstream O2 sensors are not determined to be deteriorated until deterioration thereof advances to a larger extent than in the conventional 2-O2 sensor F/B control, enabling more efficient use of the O2 sensors, as compared with the conventional 2-O2 sensor F/B control. In other words, according to the present invention, only when the controlled air-fuel ratios on the right and left bank sides deviate with respect to the stoichiometric air-fuel ratio in the same direction, or when the controlled air-fuel ratio on only one bank side deviates, correction of the KO2 value(s) based on the 2-O2 sensor F/B control is effected and at the same time the upstream O2 sensor(s) can be determined to be deteriorated.

In this connection, FIG. 9 shows the relationship between the frequency of the KO2 value obtained after the controlled air-fuel ratio is converged to the stoichiometric value by the downstream O2 sensor output and exhaust emission characteristics. As is apparent from the FIG., as the deterioration of the upstream O2 sensor advances, the frequency of the KO2 value decreases to cause exhaust emission characteristics to become degraded. The 2-O2 sensor F/B control according to the present invention, as shown by a point A, can maintain the frequency of the KO2 value higher than that obtained by the conventional 2-O2 sensor F/B control, as shown by a point B, thereby obtaining more excellent exhaust emission characteristics than by the latter. On the other hand, the KO2 value at the point B according to the conventional 2-O2 sensor F/B control is lowered in frequency, leading to a higher probability that the O2 sensor is determined to be deteriorated, as compared with the 2-O2 sensor F/B control according to the present invention.

FIG. 11 is a fragmentary block diagram showing essential parts of an internal combustion engine to which is applied an O2 sensor deterioration-detecting system according to a second embodiment of the invention. In the present embodiment, a single catalytic converter 14 is provided for all the cylinder groups and arranged in the confluent portion 13a of the exhaust passages 13R and 13L. The second embodiment also employs the same air-fuel ratio control and the same method of detecting deterioration of upstream O2 sensors as in the first embodiment.

According to the present embodiment, when upstream O2 sensors 16R and 16L arranged, respectively, on the right and left bank sides are about to become deteriorated, and at the same time their outputs deviate in the opposite directions to each other, the catalytic converter 14 causes reaction between unburnt components emitted from the right bank and oxygen molecules emitted from the left bank, whereby clean exhaust gases are emitted into the atmosphere. In the present embodiment as well, in the above-mentioned state, the downstream O2 sensor detects the stoichiometric air-fuel ratio or a ratio close thereto, so that correction of the KO2 values based on the 2-O2 sensor control is not effected. Accordingly, the frequencies of the KO2 values are not decreased and exhaust emission characteristics are not degraded.

Although in the above described embodiments, the air-fuel ratio control per cylinder group is carried out in a V-type engine, the present invention is not limited to a V-type engine, but may be also applied to other type engines, such as a straight-type four-cylinder engine having a first group consisting of #1 and #4 cylinders and a second group consisting of #2 and #3 cylinders. Further, although in the above described embodiments, the deterioration of the upstream O2 sensors 16R and 16L is detected from the inversion periods of the outputs from the upstream O2 sensors 16R and 16L, alternatively the deterioration may be detected from the frequencies of the outputs of the sensors, or from the amplitudes of the R-KO2 and L-KO2 values.

What is claimed is:

1. An oxygen sensor deterioration-detecting system for an internal combustion engine having a plurality of groups of cylinders, an exhaust system having a plurality of exhaust passages extending from respective ones of said groups of cylinders, said exhaust passages having downstream end portions thereof cojoined into a confluent portion, and catalytic exhaust gas-purifying means arranged in said exhaust system, and a plurality of upstream oxygen sensors arranged in respective ones of said exhaust passages at locations upstream of said catalytic exhaust gas-purifying means, comprising:

a single downstream oxygen sensor arranged in said confluent portion of said exhaust passages at a location downstream of said catalytic exhaust gas-purifying means, for detecting a mixed air-fuel ratio of exhaust gases emitted from said groups of cylinders;

a plurality of air-fuel ratio control means responsive to outputs from said upstream oxygen sensors and an output from said downstream oxygen sensor, for determining air-fuel ratio control amounts for respective ones of said groups of cylinders, and for controlling air-fuel ratios of air-fuel mixtures supplied into said respective ones of said groups of cylinders by the use of said air-fuel ratio control amounts determined; and oxygen sensor deterioration-detecting means for detecting deterioration of each of said upstream oxygen sensors, based on an output from said each of said upstream oxygen sensors obtained by operation of a corresponding one of said air-fuel ratio control means.

2. An oxygen sensor deterioration-detecting system as claimed in claim 1, wherein said oxygen sensor deterioration-detecting means detects deterioration of said each of said upstream oxygen sensors, based on an inversion period of the output from said each of said upstream oxygen sensors obtained by the operation of said corresponding one of said air-fuel ratio control means.

3. An oxygen sensor deterioration-detecting system as claimed in claim 2, wherein said oxygen sensor deterioration-detecting means determines that said each of said upstream oxygen sensors is deteriorated, when said inversion period of the output from said each of said upstream oxygen sensors exceeds a predetermined value.

4. An oxygen sensor deterioration-detecting system as claimed in claim 1, wherein said catalytic exhaust gas-purifying means comprises a plurality of catalytic converters arranged in respective ones of said exhaust passages.

5. An oxygen sensor deterioration-detecting system as claimed in claim 1, wherein said catalytic exhaust gas-purifying means comprises a single catalytic converter arranged in said confluent portion of said exhaust passages.

* * * * *